(12) United States Patent
Garantziotis et al.

(10) Patent No.: US 9,717,752 B2
(45) Date of Patent: Aug. 1, 2017

(54) USES OF ANTAGONISTS OF HYALURONAN SIGNALING

(71) Applicants: The United States of America, as represented by the Secretary, Department of Health and Human Services, Washington, DC (US); Duke University, Durham, NC (US); The University of North Carolina at Chapel Hill, Chapel Hill, NC (US)

(72) Inventors: Stavros Garantziotis, Chapel Hill, NC (US); John W. Hollingsworth, Durham, NC (US); Bryan P. Toole, Mt. Pleasant, SC (US); Jian Liu, Chapel Hill, NC (US)

(73) Assignees: The United States of America, as represented by the Secretary, Department of Health and Human Services, Washington, DC (US); Duke University, Durham, NC (US); The University of North Carolina at Chapel Hill, Chapel Hill, NC (US)

( * ) Notice: Subject to any disclaimer, the term of this patent is extended or adjusted under 35 U.S.C. 154(b) by 91 days.

(21) Appl. No.: 14/398,837

(22) PCT Filed: Mar. 8, 2013

(86) PCT No.: PCT/US2013/029776
§ 371 (c)(1),
(2) Date: Nov. 4, 2014

(87) PCT Pub. No.: WO2013/172923
PCT Pub. Date: Nov. 21, 2013

(65) Prior Publication Data
US 2015/0105345 A1 Apr. 16, 2015

Related U.S. Application Data

(60) Provisional application No. 61/647,101, filed on May 15, 2012.

(51) Int. Cl.
| A61K 31/715 | (2006.01) |
| A61K 31/726 | (2006.01) |
| A61K 31/727 | (2006.01) |
| A61K 31/728 | (2006.01) |
| A61K 9/00 | (2006.01) |
| A61K 31/702 | (2006.01) |

(52) U.S. Cl.
CPC ............ *A61K 31/728* (2013.01); *A61K 9/008* (2013.01); *A61K 9/0075* (2013.01); *A61K 9/0078* (2013.01); *A61K 31/702* (2013.01); *A61K 31/726* (2013.01); *A61K 31/727* (2013.01); *A61K 31/715* (2013.01)

(58) Field of Classification Search
None
See application file for complete search history.

(56) References Cited

U.S. PATENT DOCUMENTS

| 2007/0099867 A1 | 5/2007 | Asari et al. |
| 2010/0036001 A1 | 2/2010 | DeAngelis |
| 2011/0195025 A1 | 8/2011 | Kett et al. |

FOREIGN PATENT DOCUMENTS

| JP | 2010-260846 | 11/2010 |
| WO | WO 02/32406 | 4/2002 |
| WO | WO 02/102317 | 12/2002 |
| WO | WO 2004/082610 | 9/2004 |
| WO | WO 2009/124266 | 10/2009 |
| WO | WO 2010/068308 | 6/2010 |
| WO | WO 2011/156445 | 12/2011 |

OTHER PUBLICATIONS

Hess, K. et al "Inter-alpha-inhibitor binding to hyaluronan . . ." Biol. Reprod. (1999) vol. 61, pp. 436-443.*
Adair et al., "Inter-α-Trypsin Inhibitor Promotes Bronchial Epithelial Repair after Injury through Vitronectin Binding," *J. Biol. Chem.*, vol. 284:16922-16930, 2009.
Bracke et al., "Enhanced Deposition of Low-Molecular-Weight Hyaluronan in Lungs of Cigarette Smoke-Exposed Mice," *Am. J. Respir. Cell Mol. Biol.*, vol. 42:753-761, 2010.
Dentener et al., "Enhanced Levels of Hyaluronan in Lungs of Patients with COPD: Relationship with Lung Function and Local Inflammation," *Thorax*, vol. 60:114-119, 2005.
Garantziotis et al., "Hyaluronan Mediates Ozone-Induced Airway Hyperresponsiveness in Mice," *J. Biol. Chem.*, vol. 284:11309-11317, 2009.
Garantziotis et al., "TLR4 is Necessary for Hyaluronan-Mediated Airway Responsiveness after Ozone Inhalation," *Am. J. Respir. Crit. Care Med.*, vol. 181:666-675, 2010.
Klagas et al., "Decreased Hyaluronan in Airway Smooth Muscle Cells from Patients with Asthma and COPD," *Eur. Respir. J.*, vol. 34:616-628, 2009.
Lennon et al., "Role of Hyaluronan and Hyaluronan-Binding Proteins in Lung Pathobiology," *Am. J. Physiol. Lung Cell Mol. Physiol.*, vol. 301:L137-L147, 2011.
Lesley et al., "Hyaluronan Binding by Cell Surface CD44," *J. Biol. Chem.*, vol. 275:26967-26975, 2000.

(Continued)

*Primary Examiner* — Leigh C Maier
(74) *Attorney, Agent, or Firm* — Klarquist Sparkman, LLP

(57) ABSTRACT

Described herein is the finding that hyaluronan antagonists that inhibit hyaluronan signaling are capable of inhibiting airway inflammation and airway hyperresponsiveness (AHR). The present disclosure provides a method of preventing or reducing AHR in a subject suffering from or at risk for AHR by administering a hyaluronan antagonist. Also provided is a method of treating an airway disease or disorder in a subject by administering a hyaluronan antagonist. Hyaluronan antagonists include, for example, heparosan and hyaluronan oligosaccharides (oHAs). In some embodiments, the hyaluronan antagonist is administered locally to the airway, such as with an inhaler or nebulizer.

17 Claims, 6 Drawing Sheets

(56) References Cited

OTHER PUBLICATIONS

Li et al., "Hyaluronan Fragments Contribute to the Ozone-Primed Immune Response to Lipopolysaccharide," *J. Immunol.*, vol. 185:6891-6898, 2010.

Li et al., "Hyaluronan Signaling during Ozone-Induced Lung Injury Requires TLR4, MyD88, and TIRAP," *Plos One*, vol. 6:e27137, 2011.

Li et al., "Heparosan-Derived Heparan Sulfate/Heparin-Like Compounds: One Kind of Potential Therapeutic Agents," *Med. Res. Rev.*, vol. 33:665-692, 2012.

Termeer et al., "Oligosaccharides of Hyaluronan Activate Dendritic Cells via Toll-Like Receptor 4," *J. Exp. Med.*, vol. 195:99-111, 2002.

Liang et al., "Role of hyaluronan and hyaluronan-binding proteins in human asthma," *J Allergy Clin Immunol* 128:403-411, 2011.

Extended European Search Report and Written Opinion for European Application No. 13790928.9, dated Oct. 15, 2015 (6 pages).

* cited by examiner

USES OF ANTAGONISTS OF HYALURONAN SIGNALING

CROSS REFERENCE TO RELATED APPLICATIONS

This is the U.S. National Stage of International Application No. PCT/US2013/029776, filed Mar. 8, 2013, published in English under PCT Article 21(2), which claims the benefit of U.S. Provisional Application No. 61/647,101, filed May 15, 2012, which is herein incorporated by reference in its entirety.

FIELD

This disclosure concerns the use of hyaluronan antagonists, such as heparosan and hyaluronan oligosaccharides, for the reduction of airway hyperresponsiveness and treatment of airway diseases and disorders.

BACKGROUND

Airway disease, including asthma and chronic obstructive pulmonary disease (COPD), is a major health burden in the developed world. In 1999, asthma prevalence was reported at approximately 10,500,000 individuals in the U.S. (Mannino et al., *MMWR Surveill Summ* 51:1-13, 2002). The prevalence of COPD is estimated at over 23 million adults in the USA (Mannino and Braman, *Proc Am Thorac Soc* 4:502-506, 2007). In aggregate, airway disease affects up to 15% of the U.S. adult population and leads to a combined annual total of greater than 15,000,000 lost work days, greater than 1,100,000 hospitalizations, and more than 120,000 deaths, at an estimated cost burden of over $23 billion annually. A major component of airway disease is airway hyperresponsiveness (AHR), defined as the exaggerated airway constrictive response to external triggers. AHR manifests clinically as wheezing, dyspnea and cough. Since there are also asymptomatic individuals who exhibit AHR in the laboratory setting, the prevalence of AHR exceeds that of airway disease, and has been estimated at 4-35% of the general population (Jansen et al., *Respir Med* 91:121-134, 1997).

Currently, AHR treatment in airway disease is non-specific and consists of bronchodilators (adrenergic or anticholinergic) and immunosuppressants (corticosteroids). However, these treatments are fraught with significant side effects. Beta-agonist use has been linked to increased mortality from asthma in several studies, summarized in a meta-analysis (Salpeter et al., *Ann Intern Med* 144:904-912, 2006). Anticholinergic use in COPD has recently been associated with increased mortality from cardiovascular causes in these patients (Singh et al., *JAMA* 300:1439-1450, 200). Finally, corticosteroids have a number of adverse effects, even when used topically as inhalants (Dahl, *Respir Med* 100:1307-1317, 2006). Significant reasons for the side effect profile of currently existing AHR treatments are their lack of specificity and their broad, non-targeted mechanism of action. A specific, causative and physiologic treatment of AHR would therefore greatly benefit management of airway disease patients.

Hyaluronan is an abundant extracellular matrix component that has been shown to play a significant role in the response to non-infectious lung injury. Hyaluronan is a non-sulfated glycosaminoglycan that exists as a large polymer of disaccharides (D-glucuronic acid and D-N-acetylglucosamine). Short-fragment hyaluronan (sHA; also known as low molecular weight hyaluronan—LMW-HA) is released in the lung after sterile injury such as bleomycin instillation (Teder et al., *Science* 296(5565):155-158, 2002) or high-tidal-volume ventilation (Bai et al., *Am J Respir Crit. Care Med* 172(1):92-98, 2005), and can modify the tissue response to injury.

In addition, hyaluronan has been identified in airway secretions from asthmatics (Sahu and Lynn, *Biochem J* 173(2):565-568, 1978) and high molecular weight hyaluronan (HMW-HA) can attenuate the bronchoconstrictive response in exercise-induced asthma (Petrigni and Allegra, *Pulm Pharmacol Ther* 19(3):166-171, 2006). Furthermore, it has been previously demonstrated that hyaluronan mediates both airway inflammation and AHR after environmental pollutant exposure and in several mouse models of asthma (PCT Publication No. WO 2010/068308 and Garantziotis et al., *J Biol Chem* 284(17):11309-11317, 2009).

SUMMARY

Disclosed herein is the finding that a group of hyaluronan antagonists, including heparosan and hyaluronan oligosaccharides (oHAs), inhibit hyaluronan signaling leading to the inhibition of airway inflammation and AHR.

Provided herein is a method of treating an airway disease or disorder in a subject, or preventing or reducing airway hyperresponsiveness (AHR) in a subject, by selecting a subject with an airway disease or disorder, or suffering from or at risk for AHR, and administering to the subject a therapeutically effective amount of a hyaluronan antagonist. The airway disease or disorder can be an acute or chronic disease or disorder.

In some embodiments, the hyaluronan antagonist is heparosan or a hyaluronan oligosaccharide (oHA).

In some embodiments, the hyaluronan antagonist is administered by local delivery to the airway, such as by using an inhaler or nebulizer.

The foregoing and other objects, features, and advantages of the invention will become more apparent from the following detailed description, which proceeds with reference to the accompanying figures.

DETAILED DESCRIPTION

I. Abbreviations

Figure 1:
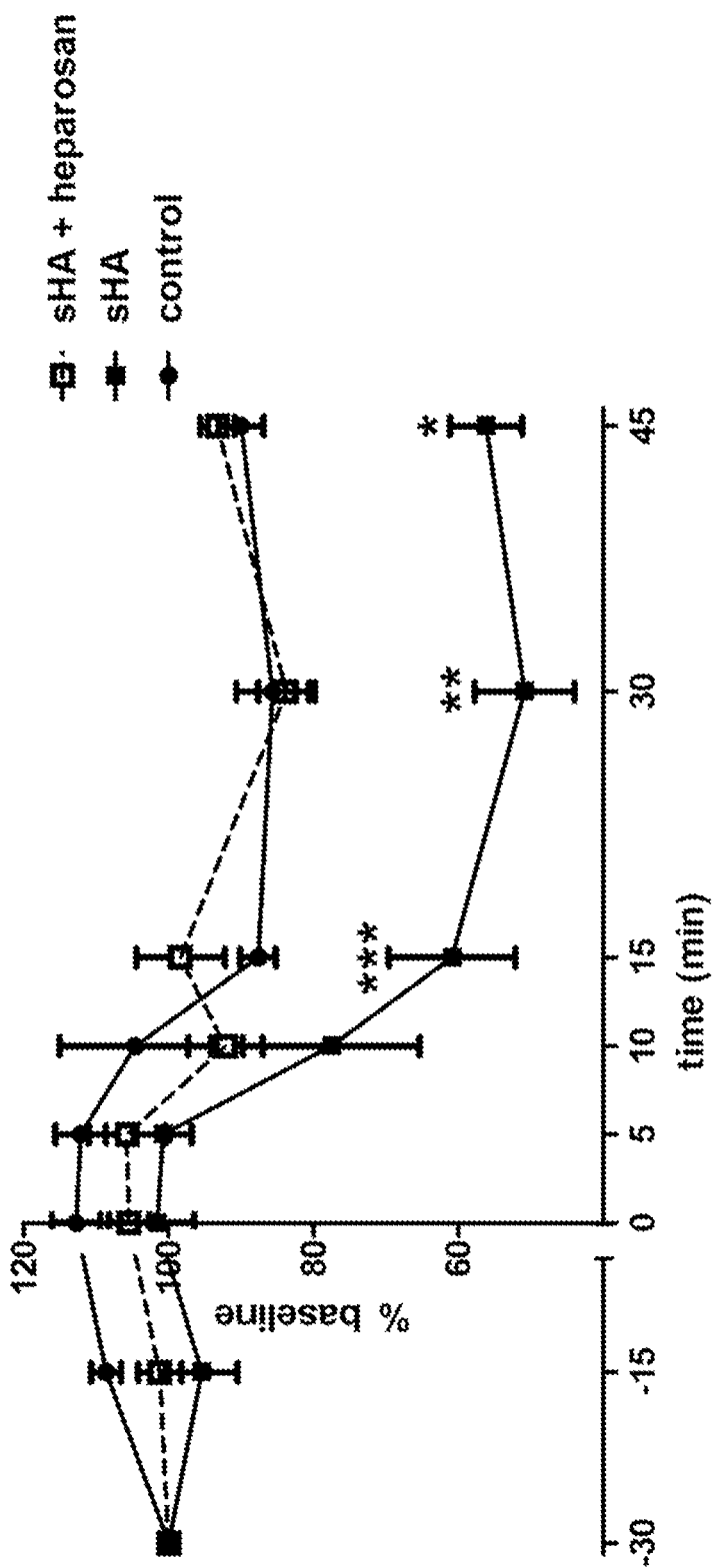
FIG. 1 is a graph showing heparosan abolished in vitro human airway smooth muscle contraction after exposure to short fragment hyaluronan (sHA) in an in vitro model of human airway smooth muscle cell (haSMC) contractility. sHA led to rapid contraction of a gel containing haSMC (filled squares). Addition of heparosan inhibited this action (open squares), and was indistinguishable from control cells (circles).

AHR airway hyperresponsiveness
BOOP bronchiolitis obliterans organizing pneumonia
CF cystic fibrosis
COPD chronic obstructive pulmonary disease
DPB diffuse panbronchiolitis
DPI dry powder inhaler
ELISA enzyme-linked immunosorbent assay
HA hyaluronan
haSMC human airway smooth muscle cell
HMW high molecular weight
LMW low molecular weight
LPS lipopolysaccharide
maSMC mouse airway smooth muscle cell
MDI metered dose inhaler
$O_3$ ozone
oHA hyaluronan oligosaccharide
OVA ovalbumin
ppm parts per million
sHA short fragment hyaluronan II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Acute: A disease or disorder of short duration, generally characterized by severe symptoms and rapid progression. This term is used in contrast to "chronic".

Administration: Administration of an active compound or composition (such as a hyaluronan antagonist), which can occur by any route known to one of skill in the art. Administration can be local or systemic. Examples of local administration (also referred to as "local delivery") include, but are not limited to, topical administration, subcutaneous administration, intramuscular administration, intrathecal administration, intrapericardial administration, intra-ocular administration, topical ophthalmic administration, or administration to the nasal mucosa or lungs by inhalational administration (for example, by aerosol delivery). In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs, such as vascular stents or other reservoirs, which release the active agents and compounds over extended time intervals for sustained treatment effects.

Systemic administration includes any route of administration designed to distribute an active compound or composition widely throughout the body via the circulatory system. Thus, systemic administration includes, but is not limited to intra-arterial and intravenous administration. Systemic administration also includes, but is not limited to, topical administration, subcutaneous administration, intramuscular administration, or administration by inhalation, when such administration is directed at absorption and distribution throughout the body by the circulatory system.

Aerosol: A gaseous suspension of fine solid or liquid particles, such as a suspension of a drug or other substance to be dispensed in a cloud or mist. Aerosol delivery refers to administration (such as to the airway) of a therapeutic agent that is formulated as an aerosol.

Airway disease or disorder: Includes any disease or disorder that affects the respiratory tract (such as the lungs, mouth, nose, pulmonary alveoli, pharynx, larynx, trachea, or bronchi). In many cases, airway diseases or disorders result in airway constriction with symptoms including wheezing, coughing and shortness of breath. In some embodiments herein, the airway disease or disorder is a chronic disorder, such as, but not limited to, asthma, chronic obstructive pulmonary disease, cystic fibrosis, obliterative bronchiolitis, diffuse panbronchiolitis or cryptogenic organizing pneumonia. In other embodiments, the airway disease or disorder is an acute disease or disorder, such as, but not limited to exercise-induced asthma, airway hyperresponsiveness, respiratory infection, acute bronchiolitis, pollution-induced airway injury, chemical-induced airway injury and ventilation-induced airway injury.

Airway hyperresponsiveness (AHR): Refers to a state that is characterized by increased susceptibility to airway narrowing (also referred to as bronchospasm, the contraction of the bronchioles or small airways), following exposure to a trigger, such as an environmental trigger (e.g., pollution or an allergen). Hyperreactivity can be assessed using constrictor agonists, such as methacholine or histamine. Subjects with AHR have a lower threshold of tolerance to constrictor agonists compared to healthy subjects. AHR is a hallmark of asthma, but also occurs in many other airway diseases such as COPD. AHR is also known as bronchial hyperresponsiveness or airway hyperreactivity.

Airway injury: Refers to any type of physical or structural damage to the airway, such as from trauma (for example, an injury to the airway resulting from intubation/ventilation) or exposure to a chemical (such as a chemical burn from ammonia or a toxic gas).

Allergen: Any substance that can produce an allergic reaction or hypersensitivity in a subject. For example, common allergens include pollen, dander, mold, dust, perfume, smoke, drugs (such as antibiotics) or particular types of food (for example, eggs, peanuts, tree nuts, milk, shellfish, fish, wheat and wheat derivatives, soy and soy derivatives, sulfites) or food components (such as gluten).

Asthma: A chronic condition involving the respiratory system in which the airways constrict, become inflamed and are lined with excessive amounts of mucus, often in response to one or more triggers. Episodes of asthma can be triggered by a number of different factors, such as exposure to an environmental stimulant, such as an allergen, environmental tobacco smoke, cold or warm air, perfume, pet dander, moist air, exercise or exertion, or emotional stress. In children, the most common triggers are viral illnesses such as those that cause the common cold. The airway narrowing that occurs in asthma causes symptoms such as wheezing, shortness of breath, chest tightness and coughing.

Bronchiolitis: Inflammation of the bronchioles, the smallest air passages of the lungs. The term often refers to acute viral bronchiolitis, a common disease in infancy, usually caused by respiratory syncytial virus or other viruses including metapneumovirus, influenza, parainfluenza, coronavirus, adenovirus and rhinovirus. Obliterative bronchiolitis (also known as bronchiolitis obliterans or constrictive bronchiolitis) is a life-threatening form of non-reversible obstructive lung disease in which the bronchioles are plugged with granulation tissue. Inflammation and scarring occur in the airways of the lung, resulting in severe shortness of breath and dry cough. Obliterative bronchiolitis has many possible causes, including collagen vascular disease, transplant rejection in organ transplant patients, viral infection (e.g., respiratory syncytial virus, adenovirus, human immunodeficiency virus or cytomegalovirus), pneumocystis pneumonia, drug reaction, complications of prematurity (bronchopulmonary dysplasia), and exposure to toxic fumes (such as diacetyl, sulfur dioxide, nitrogen dioxide, ammonia, chlorine, thionyl chloride, methyl isocyanate, hydrogen fluoride, hydrogen bromide, hydrogen chloride, hydrogen sulfide, phosgene, polyamide-amine dyes or ozone). Diffuse panbronchiolitis (DPB) is an inflammatory lung disease (considered to be a type of COPD) with no known cause. DPB is a severe, progressive form of bronchiolitis, mainly affecting the respiratory bronchioles (the section of the bronchioles involved in gas exchange). If left untreated, DPB is fatal, usually progressing to bronchiectasis, an irreversible lung condition that causes respiratory failure.

Bronchiolitis obliterans organizing pneumonia (BOOP): An inflammation of the bronchioles and surrounding tissue in the lungs. BOOP is often caused by a pre-existing chronic inflammatory disease, such as rheumatoid arthritis. BOOP can also be a side effect of certain medicinal drugs (e.g. amiodarone). In cases where no cause is found, the disease is referred to as cryptogenic organizing pneumonia. The clinical features and radiological imaging resemble infectious pneumonia. However, diagnosis is suspected after there is no response to multiple antibiotics, and blood and sputum cultures are negative for organisms. "Organizing" refers to unresolved pneumonia (in which the alveolar exudate persists and eventually undergoes fibrosis) in which fibrous tissue forms in the alveoli. The phase of resolution and/or remodeling following bacterial infections is commonly referred to as organizing pneumonia, both clinically and pathologically.

Chronic: A "chronic" disease or disorder is a condition that persists for a long period of time. Any disease or disorder that persists for at least three months is generally considered a "chronic" disease or disorder.

Chronic obstructive pulmonary disease (COPD): A disease of the lungs in which the airways become narrowed, leading to a limitation of the flow of air to and from the lungs, which causes shortness of breath. In contrast to asthma, the limitation of airflow is poorly reversible and usually gradually gets worse over time. COPD is caused by noxious particles or gases, most commonly from smoking, which trigger an abnormal inflammatory response in the lung. The inflammatory response in the larger airways is known as chronic bronchitis, which is diagnosed clinically when people regularly cough up sputum. In the alveoli, the inflammatory response causes destruction of the tissue of the lung, a process known as emphysema. The natural course of COPD is characterized by occasional sudden worsening of symptoms called acute exacerbations, most of which are caused by infections or air pollution. COPD is also known as chronic obstructive lung disease, chronic obstructive airway disease, chronic airflow limitation and chronic obstructive respiratory disease. As an example, emphysema is one type of COPD.

Cystic fibrosis (CF): A hereditary (autosomal recessive) disease affecting the exocrine (mucus) glands of the lungs, liver, pancreas, and intestines, causing progressive disability due to multisystem failure. CF is caused by a mutation in a gene called the cystic fibrosis transmembrane conductance regulator. The product of this gene is a chloride ion channel important in creating sweat, digestive juices, and mucus. Thick mucus production in CF patients results in frequent lung infections. Lung disease results from clogging the airways due to mucosa buildup and resulting inflammation. Inflammation and infection cause injury to the lungs and structural changes that lead to a variety of symptoms. In the early stages, incessant coughing, copious phlegm production and decreased ability to exercise are common. Many of these symptoms occur when bacteria that normally inhabit the thick mucus grow out of control and cause pneumonia. In later stages of CF, changes in the architecture of the lung further exacerbate chronic difficulties in breathing.

Glycosaminoglycan (GAG): Polysaccharide composed of disaccharide subunits of N-acetyl-hexosamine and hexose or hexuronic acid, with varying degrees of sulfation occurring on each subunit. GAGs include heparin, heparin sulfate, chondroitin sulfate, dermatan sulfate, and heparan sulfate.

Heparosan: A hyaluronan analogue that is a natural biosynthetic precursor of heparin and heparin sulfate. As a natural product, heparosan is non-antigenic. Heparosan is a member of the glycosaminoglycan polysaccharide family. The heparosan molecular structure $(\beta 4GlcUA-\alpha 3GlcNAc)_n$ is very similar to hyaluronan $(\beta 4GlcUA-\beta 3GlcNAc)_n$ (GlcUA=glucuronic acid, GlcNAc=N-acetyl-galactosamine) and therefore may act as a mimetic without intrinsic activity (i.e. an antagonist). In the context of the present disclosure, the heparosan can range in size from a short fragment form (12-mer to 16-mer) to a long fragment form (up to 200,000 kDa). All sizes of heparosan are contemplated for use in the methods disclosed herein. In some embodiments, the heparosan is a 12-mer (approximately 4-5 kDa). In other embodiments, the heparosan is approximately 40 kDa.

Hyaluronan antagonist: Any compound that acts against and/or blocks the action of hyaluronan. In the context of the present disclosure, hyaluronan antagonists include heparosan and hyaluronan oligosaccharides.

Hyaluronan oligosaccharide (oHA): Compounds having the same basic disaccharide structure (N-acetyl glucosamine and glucuronic acid) as native hyaluronan, but distinguishable from both high molecular weight hyaluronan (HMW-HA) and low molecular weight (LMW)-HA (also shown as short fragment HA or sHA) by their small size. The molecular weight of native hyaluronan (including both HMW-HA and LMW-HA) ranges from approximately 50 kD to 10,000 kD, and is composed of hundreds to thousands (up to 25,000) of disaccharide units. In contrast, oHAs are defined as having 2-12 disaccharide units, with a molecular weight of <5 kD.

Inhaler: An apparatus for administering vapor or volatilized medications by inhalation. Inhalers are often used to administer medication locally to the airway, for example to treat asthma. In some examples, the inhaler is a dry powder inhaler. In other examples, the inhaler is a metered-dose inhaler.

Exertion: Expenditure of energy by skeletal muscles, such as during exercise.

Nebulizer: A device that turns liquid forms of medicine into a fine spray (aerosol) that can be inhaled, especially for delivering medication to the deep part of the respiratory tract.

Particulate matter: Material suspended in the air in the form of minute solid particles or liquid droplets.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In some embodiments, the pharmaceutically acceptable carrier is suitable for delivery to an airway. Carriers for airway delivery are well known in the art and are discussed below.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Stress: A state of difficulty, strain or pressure. Stress can be mental, emotional and/or physical.

Subject: Living multi-cellular vertebrate organisms, a category that includes both human and non-human mammals.

Therapeutically effective amount: A quantity of a specified pharmaceutical agent sufficient to achieve a desired effect in a subject, or in a cell, being treated with the pharmaceutical agent. For example, this can be the amount of hyaluronan antagonist useful for preventing or reducing AHR. The effective amount of the pharmaceutical agent will be dependent on several factors, including, but not limited to the subject or cells being treated, and the manner of administration of the therapeutic composition.

Trigger: As used herein, a "trigger" for AHR is any type of environmental, chemical or physical substance or perturbation that causes or increases the risk of AHR. In some examples, an environmental trigger is pollution (such as ozone or particulate matter) or an allergen. In some examples, a chemical trigger is exposure to ammonia or another toxic gas. In some examples, the physical trigger is stress or exertion.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Disclosed herein is the finding that a group of hyaluronan antagonists, including heparosan and hyaluronan oligosaccharides (oHAs), inhibit hyaluronan signaling leading to the inhibition of airway inflammation and AHR.

Provided herein is a method of treating an airway disease or disorder in a subject. The method includes selecting a subject with an airway disease or disorder and administering to the subject a therapeutically effective amount of a hyaluronan antagonist, thereby treating the airway disease or disorder. In some embodiments, the hyaluronan antagonist comprises heparosan or a hyaluronan oligosaccharide (oHA).

In some embodiments, the airway disease or disorder is a chronic disease or disorder. Chronic airway diseases and disorders include, but are not limited to, asthma, chronic obstructive pulmonary disease, cystic fibrosis, obliterative bronchiolitis, diffuse panbronchiolitis and cryptogenic organizing pneumonia.

In other embodiments, the airway disease or disorder is an acute disease or disorder. Acute airway diseases and disorders include, but are not limited to, exercise-induced asthma, respiratory infection, acute bronchiolitis, airway hyperresponsiveness, pollution-induced airway injury, chemical-induced airway injury and ventilation-induced airway injury.

Also provided herein is a method of preventing or reducing airway hyperresponsiveness (AHR) in a subject. The method includes selecting a subject suffering from or at risk for AHR, and administering to the subject a therapeutically effective amount of a hyaluronan antagonist, thereby preventing or reducing AHR. In some embodiments, the hyaluronan antagonist comprises heparosan or an oHA.

In some embodiments, the subject suffers from asthma or COPD.

In some embodiments, AHR is triggered by an environmental trigger, a chemical trigger, exertion or stress. In some examples, the environmental trigger is ozone, particulate matter or an allergen. In some examples, the chemical trigger is ammonia or another toxic chemical. Respiratory infection (such as viral infection), which often causes bronchiolitis, can also result in AHR. Thus, a subject with a respiratory infection can also be selected for treatment with a hyaluronan antagonist. Hyaluronan antagonists can also be used to treat patients having an airway injury, such as an injury resulting from intubation/ventilation or a chemical burn.

In particular examples, the hyaluronan antagonist is administered prophylactically prior to exposure to the trigger. In other specific examples, the hyaluronan antagonist is administered therapeutically after the onset of symptoms.

The hyaluronan antagonist can be administered in a single dose or in multiple doses. An appropriate dose and dosing schedule can be determined by a skilled practitioner. In some examples, the hyaluronan antagonist is administered daily. In other examples, the hyaluronan antagonist is administered as need to prevent or treat the airway disease or disorder or AHR.

In some embodiments, the dose of heparosan is about 1 µg to about 1 mg, such as about 5 µg to about 500 µg, or about 10 µg to about 250 µg, or about 50 µg to about 100 µg, or about 1 µg to about 100 µg, or about 10 µg to about 100 µg, or about 25 µg to about 100 µg. In particular examples, the dose of heparosan is about 1, about 5, about 10, about 25, about 50, about 75 or about 100 µg. In specific non-limiting examples, heparosan is administered daily at a dose of about 1 µg to about 1 mg, such as about 5 µg to about 500 µg, or about 10 µg to about 250 µg, or about 50 µg to about 100 µg, or about 1 µg to about 100 µg, or about 10 µg to about 100 µg, or about 25 µg to about 100 µg.

In some embodiments, the dose of oHA is about 1 µg to about 1 mg, such as about 5 µg to about 500 µg, or about 10 µg to about 250 µg, or about 50 µg to about 100 µg, or about 1 µg to about 100 µg, or about 10 µg to about 100 µg, or about 25 µg to about 100 µg. In particular examples, the dose of oHA is about 1, about 5, about 10, about 25, about 50, about 75 or about 100 µg. In specific non-limiting examples, oHA is administered daily at a dose of about 1 µg to about 1 mg, such as about 5 µg to about 500 µg, or about 10 µg to about 250 µg, or about 50 µg to about 100 µg, or about 1 µg to about 100 µg, or about 10 µg to about 100 µg, or about 25 µg to about 100 µg.

The hyaluronan antagonist can be administered to the subject using any suitable route of administration. In some embodiments of the methods disclosed herein, administration of the hyaluronan antagonist comprises local delivery to the airway. In some examples, local delivery comprises aerosol delivery. In particular examples, the hyaluronan antagonist is administered by aerosol using an inhaler, such as a dry powder inhaler or a metered-dose inhaler. In other specific examples, the hyaluronan antagonist is administered by aerosol using a nebulizer.

IV. Aerosol Administration of Hyaluronan Antagonists

In some cases, it is desirable to deliver a hyaluronan antagonist locally to the airway to limit potential side effects that may result from inhibiting hyaluronan in other cells or tissues. Therefore, in some embodiments, the hyaluronan antagonist is administered to the subject in need of treatment by aerosol delivery. Aerosol delivery is generally of lower risk than systemic delivery as it allows for administration of smaller doses of the inhaled medication with equal or greater therapeutic effect and minimal adverse effects. The therapeutic efficiency of therapeutic agents (such as compositions comprising a hyaluronan antagonist) administered by aerosolization depends not only on the pharmacological properties of the therapeutic agents themselves, but also on the characteristics of the delivery device. The characteristics of the delivery device influence the amount of drug deposited in the lungs and the pattern of drug distribution in the airways.

A. Aerosols

Aerosols are airborne suspensions of fine particles. The particles may be solids or liquids. Aerosol particles are heterodisperse (i.e. the particles include a range of sizes) and aerosol particle size distribution is best described by a log normal distribution. Particles tend to settle (sediment), adhere to each other (coagulate), and adhere to structures such as tubing and mucosa (deposit). The particles delivered by aerosol can be conveniently characterized on the basis of their aerodynamic behavior. One parameter is the mass median aerodynamic diameter (MMAD). By definition, a particle distribution with an MMAD of 1 µM has the same average rate of settling as a droplet of unit density and 1 µM diameter.

The size of an aerosol particle, as well as variables affecting the respiratory system, influence the deposition of inhaled aerosols in the airways. For example, particles larger than 10 µM in diameter are unlikely to deposit in the lungs. However, particles smaller than 0.5 µM are likely to reach the alveoli or may be exhaled. Therefore, particles that have a diameter of between 1 µM and 5 µM are most efficiently deposited in the lower respiratory tract. Particles of these sizes are most efficient for the delivery of therapeutic agents for some airway diseases, such as asthma.

The percentage of the aerosol mass contained within respirable droplets (i.e., droplets with a diameter smaller than 5 µM), depends on the inhalation device being used. Slow, steady inhalation increases the number of particles that penetrate the peripheral parts of the lungs. As the inhaled volume is increased, the aerosol can penetrate more peripherally into the bronchial tree. A period of breath-holding, on completion of inhalation, enables those particles that have penetrated to the lung periphery to settle into the airways via gravity. Increased inspiratory flow rates, typically observed in patients with acute asthma, result in increased losses of inhaled drug. This occurs because aerosol particles impact in the upper airway and at the bifurcations of the first few bronchial divisions. Other factors associated with pulmonary airway disease may also alter aerosol deposition. Airway obstruction and changes in the pulmonary parenchyma are often associated with pulmonary deposition in the peripheral airways in patients with asthma.

With aerosol delivery, the nose efficiently traps particles before their deposition in the lung. Therefore, mouth breathing of the aerosolized particles is preferred. The aerosolized particles are lost from many sites. Generally, the amount of the nebulized dose reaching the small airways is less than about 15%. In many cases, approximately 90% of the inhaled dose is swallowed and then absorbed from the gastrointestinal tract. The small fraction of the dose that reaches the airways is also absorbed into the blood stream. The swallowed fraction of the dose is, therefore, absorbed and metabolized in the same way as an oral formulation, while the fraction of the dose that reaches the airways is absorbed into the blood stream and metabolized in the same way as an intravenous dose.

B. Inhalation Devices

Typically, aerosol delivery is accomplished using an inhaler, such as a metered dose inhaler (MDI) or a dry powder inhaler (DPI), or a nebulizer. Inhalers and nebulizers are devices for administering aerosolized therapeutic agents to a subject via inhalation. Ultrasonic, electrical, pneumatic, hydrostatic or mechanical forces (such as compressed air or by other gases) can drive these devices.

A nebulizer delivers fine mists of liquids, suspensions or dispersions for inhalation. A nebulizer can be a mechanical powder device which disperses fine powder into a finer mist using leverage or piezo electric charges in combination with suitably manufactured porous filter discs, or as formulations that do not aggregate in the dose chamber. Propellants can be used to spray a fine mist of the product such as fluorochlorocarbons, fluorocarbons, nitrogen, carbon dioxide, or other compressed gases. Nebulized aerosols are particularly useful for children under five years of age and in the treatment of severe asthma where respiratory insufficiency may impair inhalation from an MDI or dry powder inhaler.

A nebulizer type inhalation delivery device can contain a therapeutic agent (such as a hyaluronan antagonist) as a solution, usually aqueous, or a suspension. In generating the nebulized spray of the therapeutic agent for inhalation, the nebulizer type delivery device can be driven ultrasonically, by compressed air, by other gases, electronically or mechanically. The ultrasonic nebulizer device generally works by imposing a rapidly oscillating waveform onto the liquid film of the formulation via an electrochemical vibrating surface. At a given amplitude, the waveform becomes unstable, disintegrates the liquids film, and produces small droplets of the formulation. The nebulizer device driven by air or other gases operates on the basis that a high pressure gas stream produces a local pressure drop that draws the liquid formulation into the stream of gases via capillary action. This fine liquid stream is then disintegrated by shear forces. The nebulizer can be portable and hand held in design, and can be equipped with a self-contained electrical unit. The nebulizer device can consist of a nozzle that has two coincident outlet channels of defined aperture size through which the liquid formulation can be accelerated. This results in impaction of the two streams and atomization of the formulation. The nebulizer can use a mechanical actuator to force the liquid formulation through a multiorifice nozzle of defined aperture size to produce an aerosol of the formulation for inhalation. In the design of single dose nebulizers, blister packs containing single doses of the formulation can be employed.

Formulations suitable for use with a nebulizer, either jet or ultrasonic, can include a compound (such as a hyaluronan antagonist) dissolved in water at a concentration of about 0.1 to 25 mg of biologically active compound per mL of solution. The formulation can also include a buffer and a simple sugar (such as for protein stabilization and regulation of osmotic pressure). The nebulizer formulation can also contain a surfactant, to reduce or prevent surface induced aggregation of the compound (such as a protein) caused by atomization of the solution in forming the aerosol (U.S. Patent Application Publication No. 2007/0065367).

A metered dose inhalator (MDI) can also be employed as the aerosol delivery device. Because of their convenience and effectiveness, MDIs are probably the most widely used therapeutic aerosol used for inhaled drug delivery to outpatients. MDIs are pressurized and their basic structure consists of a metering valve, an actuator and a container. A propellant is used to discharge the formulation from the device. The composition can include particles of a defined size suspended in the pressurized propellant liquid, or the composition can be in a solution or suspension of pressurized liquid propellant. The propellants used are primarily atmospheric friendly hydrofluorocarbons. Traditional chlorofluorocarbons, such as CFC-1, -11, -12 and -114, are used only when essential. The device of the inhalation system can deliver a single dose (such as by a blister pack), or it can be multi-dose in design. To ensure accuracy of dosing, the delivery of the formulation can be programmed via a microprocessor to occur at a certain point in the inhalation cycle. In some cases, the MDI can be portable and hand held.

For optimal pulmonary drug deposition, the medication should be released at the beginning of a slow inspiration that lasts about five seconds and is followed by 10 seconds of breath-holding. Several inhalation aids have been designed to improve the effectiveness of MDIs. These are most useful in patients who have poor hand-to-breath coordination. A short tube (for example, cones or spheres) may be used to direct the aerosol straight into the mouth or collapsible bags can act as an aerosol reservoir holding particles in suspension for three to five seconds, during which time the patient can inhale the drug. However, when any of these devices is used, aerosol velocity upon entering the oropharynx is decreased and drug availability to the lungs and deposition in the oropharynx is decreased.

Formulations for use with a MDI device generally includes a finely divided powder containing the compound (such as a hyaluronan antagonist) suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant (U.S. Patent Application Publication No. 2007/0065367).

A dry powder inhalator (DPI) also can be used as the aerosol delivery device. DPIs are often used to deliver agents to patients who have difficulty using a MDI (for example, children and elderly patients). The basic design of a DPI includes a metering system, a powdered composition and a method to disperse the composition. Forces like rotation and vibration can be used to disperse the composition. The metering and dispersion systems can be mechanically or electrically driven and can be microprocessor-programmable. The device can be portable and hand held. The inhalator can be multi- or single-dose in design and use such options as hard gelatin capsules or blister packages for accurate unit doses. The therapeutic composition (such as a composition comprising a hyaluronan antagonist) can be dispersed from the device by passive inhalation (such as the patient's own inspiratory effort), or an active dispersion system can be employed. The dry powder of the therapeutic composition can be sized via processes such as jet milling, spray dying and supercritical fluid manufacture. Acceptable excipients such as the sugars mannitol and maltose can be used in the preparation of the powdered formulations.

Formulations for dispensing from a powder inhaler device may comprise a finely divided dry powder containing the compound (such as a hyaluronan antagonist) and can also include a bulking agent, such as lactose, sorbitol, sucrose, or mannitol in amounts which facilitate dispersal of the powder from the device, for example, 50 to 90% by weight of the formulation. The compound can be prepared in particulate form with an average particle size of less than 10 μM, such as 0.5 to 5 μM, for delivery to the distal lung (U.S. Patent Application Publication No. 2007/0065367).

Exemplary airway delivery methods, inhalation devices and formulations are known in the art (see, for example, U.S. Patent Application Nos. 2004/0009126 and 2007/0065367).

V. Methods for Evaluating Airway Hyperresponsiveness (AHR)

Airway hyperresponsiveness (AHR) refers to an abnormality of the airways that allows the airways to narrow too easily and/or too much in response to a stimulus capable of inducing airflow limitation (either irreversible or reversible airflow limitation). AHR can be a functional alteration of the respiratory system resulting from inflammation in the airways or airway remodeling (e.g., such as by collagen deposition). AHR can be caused by, for example, collagen deposition, bronchospasm, airway smooth muscle hypertrophy, airway smooth muscle contraction, mucous secretion, cellular deposits, epithelial destruction, alteration to epithelial permeability, alterations to smooth muscle function or sensitivity, abnormalities of the lung parenchyma and infiltrative diseases in and around the airways. Many of these causative factors can be associated with inflammation. AHR can be triggered in a patient with a condition associated with the above causative factors by exposure to a provoking agent or stimulus, also referred to as an AHR provoking stimulus. Such stimuli include, but are not limited to, allergens, methacholine, histamines, leukotrienes, saline, hyperventilation, exercise, sulfur dioxide, adenosine, propranolol, cold air, antigens, bradykinin, acetylcholine, prostaglandin, ozone, environmental air pollutants and combinations thereof. The present disclosure concerns airway hyperresponsiveness associated with any respiratory condition, or any airway disease or disorder.

Methods of measuring AHR are well known in the art. Exemplary methods of measuring AHR are described below and in Examples 1 and 2. AHR can be measured by a stress test that includes measuring a subject's respiratory system function in response to a provoking agent (such as a stimulus). AHR can be measured as a change in respiratory function from baseline plotted against the dose of a provoking agent. Respiratory function can be measured by, for example, spirometry, plethysmograph, peak flows, symptom scores, physical signs (e.g., respiratory rate), wheezing, exercise tolerance, use of rescue medication (e.g., bronchodilators), cough and blood gases. In humans, spirometry can be used to gauge the change in respiratory function in conjunction with a provoking agent, such as methacholine or histamine. Spirometry is generally performed by asking a subject to take a deep breath and blow, as long, as hard and as fast as possible into a gauge that measures airflow and volume. The volume of air expired in the first second is known as forced expiratory volume ($FEV_1$) and the total amount of air expired is known as the forced vital capacity (FVC). In humans, normal predicted $FEV_1$ and FVC are available and standardized according to weight, height, sex and race. An individual free of disease has an $FEV_1$ and a FVC of at least about 80% of normal predicted values for a particular person and a ratio of $FEV_1$/FVC of at least about 80%. Values are determined before (e.g., representing a subject's resting state) and after (e.g., representing a subject's higher lung resistance state) inhalation of the provoking agent. The position of the resulting curve indicates the sensitivity of the airways to the provoking agent.

The effect of increasing doses or concentrations of the provoking agent on lung function can be determined by measuring the forced expired volume in 1 second ($FEV_1$) and $FEV_1$ over forced vital capacity ($FEV_1$/FVC ratio) of the subject challenged with the provoking agent. In humans, the dose or concentration of a provoking agent (e.g., methacholine or histamine) that causes a 20% fall in $FEV_1$ ($PC_{20}FEV_1$) is indicative of the degree of AHR. $FEV_1$ and FVC values can be measured using methods known to those of skill in the art.

Pulmonary function measurements of airway resistance ($R_L$) and dynamic compliance ($C_{dyn}$ or $C_L$) and hyperresponsiveness can be determined by measuring transpulmonary pressure as the pressure difference between the airway opening and the body plethysmograph. Volume is the calibrated pressure change in the body plethysmograph and flow is the digital differentiation of the volume signal. Resistance ($R_L$) and compliance ($C_L$) are obtained using methods known to those of skill in the art (e.g., such as by using a recursive least squares solution of the equation of motion). Measuring the airway resistance ($R_L$) value in a non-human mammal (e.g., a mouse) can be used to diagnose airflow obstruction similar to measuring the $FEV_1$ and/or $FEV_1$/FVC ratio in a human.

A variety of provoking agents are useful for measuring AHR values. Suitable provoking agents include direct and indirect stimuli, and are typically provoking agents that trigger AHR in vivo. Exemplary provoking agents include, for example, allergens, methacholine, histamine, organic irritants, irritating gases and chemicals, leukotrienes, saline, hyperventilation, exercise, sulfur dioxide, adenosine, propranolol, cold air, antigens, bradykinin, acetylcholine, prostaglandin, ozone, environmental air pollutants and combinations thereof. In some instances, for experimental induction of AHR, methacholine is used as a provoking agent. Concentrations of methacholine to use in a concentration-response curve can vary, but are typically between about 0.001 and about 100 milligram per milliliter (mg/ml). In some examples, the concentrations of methacholine in a concentration-response curve are between about 0.01 and about 50 mg/ml, or between about 0.02 and about 25 mg/ml. When methacholine is used as a provoking agent, the degree of AHR can be defined by the provocative concentration of methacholine needed to cause a 20% drop of the $FEV_1$ of a mammal ($PC_{20methacholine}FEV_1$). For example, in humans and using standard protocols in the art, a normal person typically has a $PC_{20methacholine}FEV_1 > 8$ mg/ml of methacholine. Thus, in some instances in humans, AHR can be defined as $PC_{20methacholine}FEV_1 < 8$ mg/ml of methacholine.

Respiratory function can also be evaluated with a variety of static tests that include measuring a subject's respiratory system function in the absence of a provoking agent. Examples of static tests include, for example, spirometry, plethysmography, peak flows, symptom scores, physical signs (e.g., respiratory rate), wheezing, exercise tolerance, use of rescue medication (e.g., bronchodilators), blood gases and cough. Evaluating pulmonary function in static tests can be performed by measuring, for example, total lung capacity (TLC), thoracic gas volume (TgV), functional residual capacity (FRC), residual volume (RV) and specific conductance (SGL) for lung volumes, diffusing capacity of the lung for carbon monoxide (DLCO), arterial blood gases, including pH, $P_{O2}$ and $P_{CO2}$ for gas exchange. Both $FEV_1$ and $FEV_1/FVC$ can be used to measure airflow limitation. If spirometry is used in humans, the $FEV_1$ of an individual can be compared to the $FEV_1$ of predicted values. Predicted $FEV_1$ values are available for standard normograms based on the subject's age, sex, weight, height and race. A normal human subject typically has an $FEV_1$ at least about 80% of the predicted $FEV_1$ for the subject. Airflow limitation results in a $FEV_1$ or FVC of less than 80% of predicted values. An alternative method to measure airflow limitation is based on the ratio of $FEV_1$ and FVC ($FEV_1/FVC$). Disease free individuals are defined as having a $FEV_1/FVC$ ratio of at least about 80%. Airflow obstruction causes the ratio of $FEV_1/FVC$ to fall to less than 80% of predicted values. Thus, in some instances a subject having airflow limitation can be defined by an $FEV_1/FVC$ less than about 80%.

In the context of the present disclosure, reducing AHR refers to any measurable reduction in AHR and/or any reduction of the occurrence or frequency with which AHR occurs in a subject. A reduction in AHR can be measured using any of the above-described techniques, a technique described in Example 1 or Example 2, or any other suitable method known in the art. In some cases, AHR is reduced to an extent that the subject no longer suffers discomfort and/or altered function resulting from or associated with AHR. Also in the context of the present disclosure, preventing AHR refers to preventing or stopping the induction of AHR before biological characteristics of AHR can be substantially detected or measured in a subject.

The following examples are provided to illustrate certain particular features and/or embodiments. These examples should not be construed to limit the disclosure to the particular features or embodiments described.

EXAMPLES

Example 1: Heparosan Inhibits Airway Smooth Muscle Contraction In Vitro and AHR In Vivo in Mouse Models of Airway Disease This example describes the finding that heparosan inhibits human airway smooth muscle contraction in vitro after exposure to sHA. This example further shows that heparosan prevents or reduces AHR in vivo in murine models of asthma and environmental pollutant exposure. The heparosan used in the studies described below was approximately 40 kDa.

Methods

Gel Contraction

The in vitro effect of heparosan on human airway smooth muscle cells (ASMC) was tested in 3-dimensional, collagen-hyaluronan gels. Collagen-only gels were used as controls. Human ASMC ($6 \times 10^5$ cells/ml) in basal media were seeded into the gel solution and incubated up to 36 hours at 37° C. in 5% $CO_2$. Gels were scanned at varying time intervals to monitor gel contraction. After 24 hours, the gels were fixed with 4% paraformaldehyde and stained with phalloidin and DAPI. In some experiments, the ROCK inhibitor Y-27632 was added to the gel. Change in gel area was measured by NIH Image J software.

Airway Physiology

For studies of airway physiology, anesthesia was achieved with 60 mg/kg of pentobarbital sodium i.p., neuromuscular blockade with 0.8 ml/kg pancuronium bromide, and ventilation with a computer-controlled small animal ventilator (FlexiVent™, SCIREQ, Montreal, QC, Canada), with a tidal volume of 7.5 ml/kg and a positive end-expiratory pressure of 3 cm $H_2O$. Measurements of respiratory mechanics were made by the forced oscillation technique. Response to aerosolized methacholine (0, 10 mg/ml, 25 mg/ml, and 100 mg/ml) was determined by resistance measurements every 30 seconds for 5 minutes, ensuring the parameters calculated had peaked. The resistance measurements were then averaged at each dose and graphed ($R_T$, measured in cm $H_2O$/ml/s) along with the initial baseline measurement.

Animal Models of AHR

In the following studies to evaluate the effect of heparosan, mice were exposed to one of several agents: sHA (50 µl of a 1 mg/ml sHA solution in PBS—sonicated Healon, AMO Inc., Santa Ana, Calif.); 1 ppm ozone ($O_3$) for 4 hours; or inhaled OVA (sensitization with i.p. injection of 10 µg OVA (Sigma, St. Louis, Mo.), adsorbed to 2 mg of alum adjuvant (Pierce Biotechnology, Inc., Rockford, Ill.) diluted in saline on days 0 and 7, 60 minutes inhaled exposure to 1% OVA aerosol on days 14 and 15). Mice were phenotyped for AHR at typical time points for each of these exposures: 2 hours after sHA instillation; 24 hours after ozone exposure; and 48 hours after second OVA exposure. Thirty minutes prior to phenotyping, mice received appropriate treatment (saline, heparosan or heparin) by oropharyngeal aspiration. Mice received 50 µl of a 1-2 mg/ml solution of heparosan or heparin (or 50 µl of saline as a control). Phenotyping was with invasive airway pressure measurements (FlexiVent™).

Results

The effects of heparosan and heparin on airway contractility were tested in 3-dimensional, collagen-hyaluronan gels, an in vitro model of human ASMC contractility. As shown in FIG. 1, short fragment hyaluronan (sHA) led to rapid contraction of a gel containing human ASMC. Addition of heparosan inhibited this action, and was indistinguishable from control cells. These results indicated that heparosan abolishes human airway smooth muscle contraction in vitro after exposure to sHA.

Figure 2:
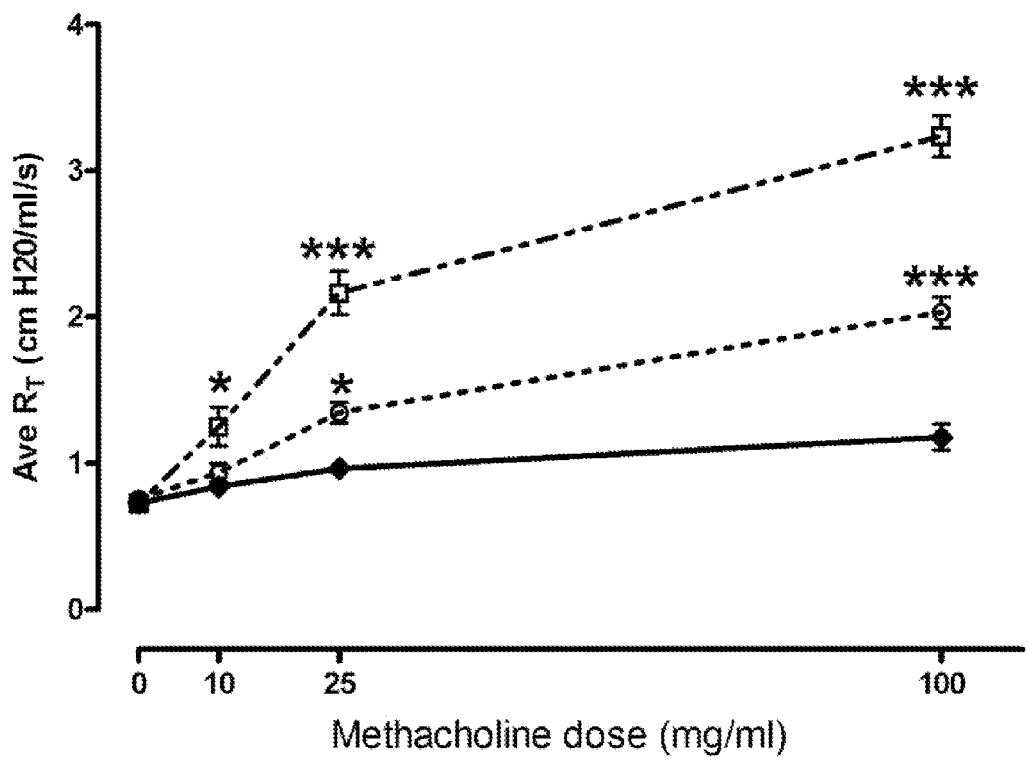
FIG. 2 is a graph showing heparosan, but not heparin, abolished AHR after in vivo exposure to sHA in an in vivo model of airway contraction. Anesthetized mice received instilled sHA solution, with added saline, heparosan or heparin. Airway resistance was measured directly in the airways. The y-axis of the graph depicts airway resistance, the x-axis depicts dose levels of methacholine, a commonly used airway constrictor. Addition of heparosan to sHA decreased the development of airway resistance (filled diamonds), compared to sHA with saline (open circles), while heparin increased the development of airway resistance (open squares).

The effects of heparosan and heparin on AHR were evaluated in an in vivo model of airway contraction to sHA. Anesthetized mice received instilled sHA solution, with added saline, heparosan or heparin. Airway resistance was measured directly in the airways. FIG. 2 shows airway resistance at various doses of methacholine (a commonly used airway constrictor) following exposure to sHA. Addition of heparosan to sHA decreased the development of airway resistance, compared to sHA with saline, while heparin increased the development of airway resistance. These results demonstrate that heparosan, but not heparin, abolishes AHR in vivo exposure to sHA.

Figure 3:
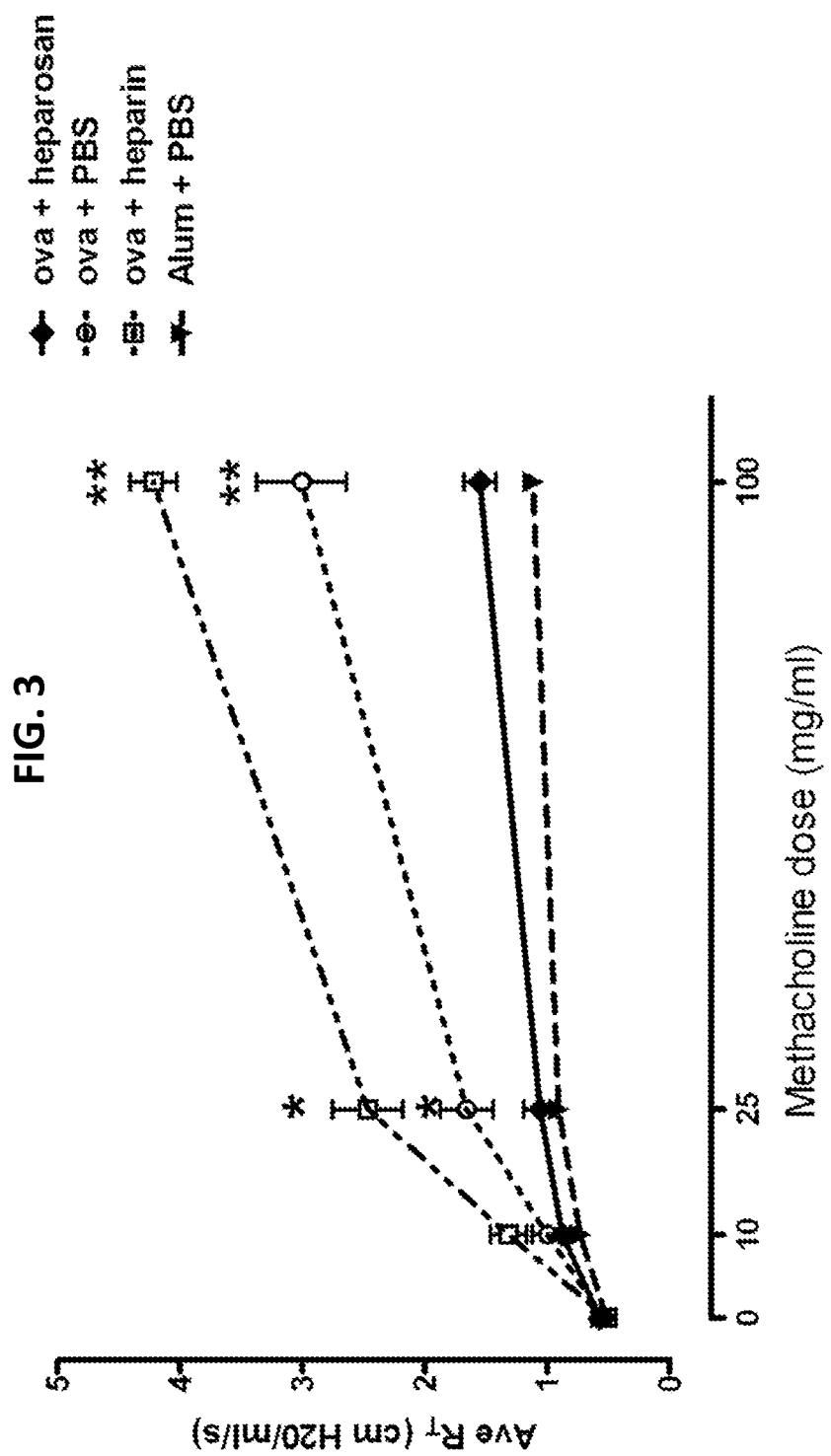
FIG. 3 is a graph showing heparosan, but not heparin, abolished inflammatory AHR when given 48 hours after exposure in a murine model of airway contraction in allergic asthma. Mice were sensitized to ovalbumin (ova) and then received inhaled ovalbumin. Measurement of airway resistance showed that heparosan, even when given 48 hours after the exposure, led to decreased airway resistance (filled diamonds) compared to saline placebo treatment (open circles), while heparin increased the development of airway resistance (open squares). The heparosan effect is indistinguishable from sham-treated (naïve) mice (filled triangles). $*=p<0.01$ compared to heparosan; $**=p<0.001$ compared to heparosan (ANOVA with Dunnett's test).

Next, heparosan and heparin were tested in a murine model of airway contraction in allergic asthma. Mice were sensitized to ovalbumin (ova) and then received inhaled ovalbumin. This typically leads to airway inflammation and bronchial constriction, and is an accepted model of allergic asthma. Measurement of airway resistance showed that heparosan, even when given 48 hours after the exposure, led to decreased airway resistance compared to saline placebo treatment, while heparin increased the development of airway resistance (FIG. 3). The heparosan effect is indistinguishable from sham-treated (naïve) mice. These results indicate that heparosan, but not heparin, abolishes inflammatory AHR in an in vivo model of allergic asthma.

Figure 4:
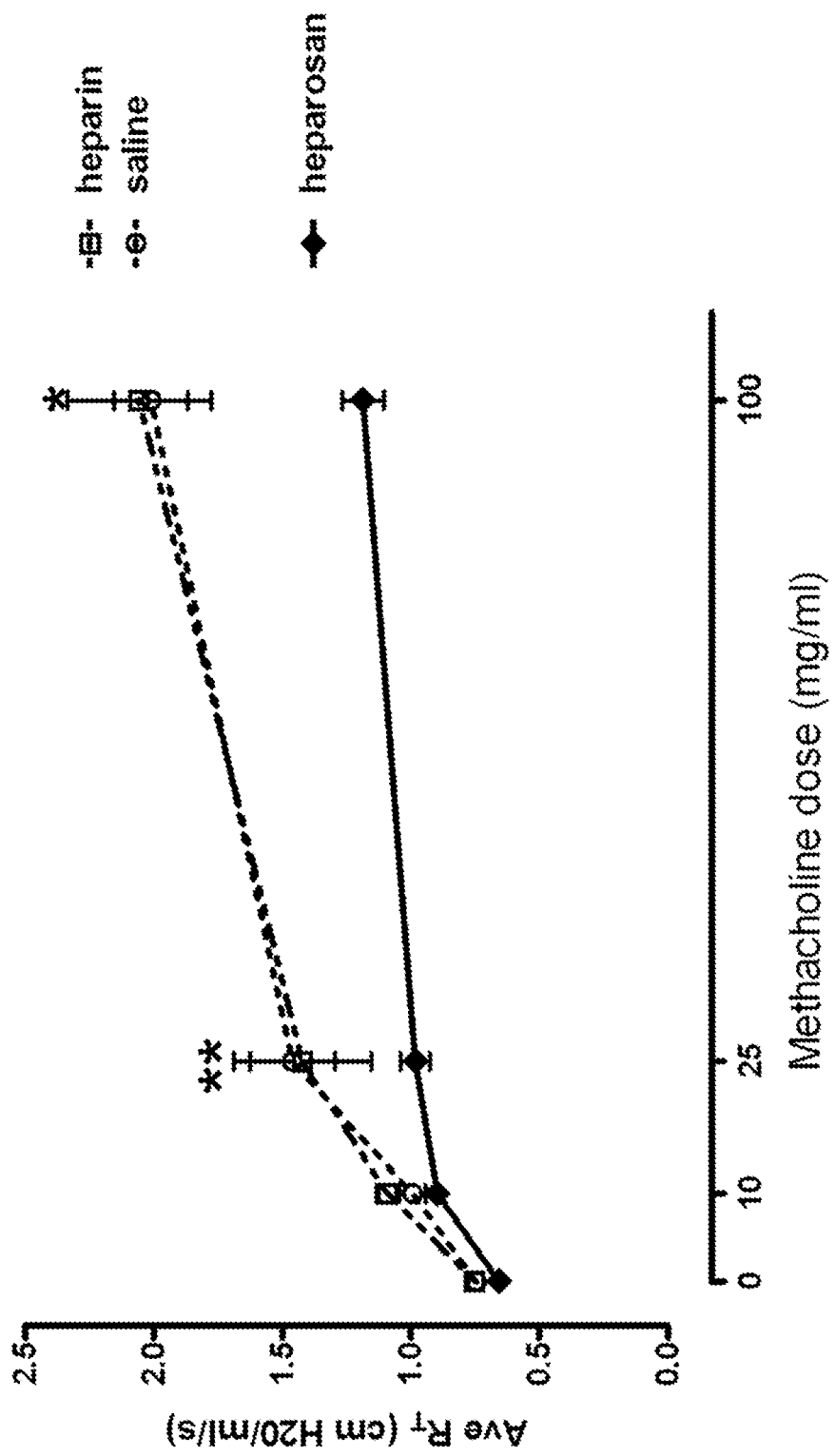
FIG. 4 is a graph showing heparosan, but not heparin, abolished inflammatory AHR when administered 24 hours after ozone exposure in a murine model of airway contraction after exposure to a pollutant. Mice were exposed to the common pollutant ozone, which in humans and mice leads to airway injury, inflammation and bronchial constriction. Measurement of airway resistance showed that heparosan, even when given 24 hours after the exposure, led to decreased airway resistance (filled diamonds) compared to saline placebo treatment (open circles). Heparin had no effect on airway resistance beyond saline.

The effect of heparosan and heparin were also tested in a murine model of environmental pollution exposure. Mice were exposed to the common pollutant ozone, which in humans and mice leads to airway injury, inflammation and bronchial constriction. As shown in FIG. 4, measurement of airway resistance showed that heparosan, even when given 24 hours after the exposure, led to decreased airway resistance compared to saline placebo treatment. Heparin had no effect on airway resistance beyond saline. These results demonstrate that heparosan, but not heparin, abolishes inflammatory AHR when administered after environmental pollutant exposure in a murine model of airway contraction.

Example 2: Hyaluronan Oligosaccharides (oHAs) Inhibit Tracheal Ring Contractility In Vitro and Inflammatory AHR In Vivo This example describes the finding that administration of heparosan ameliorates tracheal ring contractility in vitro following exposure to sHA. This data presented in this example further show that heparosan inhibits inflammatory AHR in vivo in a murine model of endotoxin exposure.

Methods

Tracheal Ring Assay

Airway smooth muscle reactivity was assessed in temperature-controlled (37° C.) organ baths containing Krebs-Henseleit buffer solution of the following composition: 118 mM NaCl, 4.7 mM KCl, 2.5 mM $CaCl_2$, 1.2 mM $MgSO_4$, 25 mM $NaHCO_3$, 1.2 mM $KH_2PO_4$, and 11.1 mM glucose, continuously bubbled with 5% $CO_2$ and 95% $O_2$. Tracheal segments were mounted in organ baths between two metal hooks and connected to a K30 force displacement transducer under approximately 5-mN resting tension. Isometric contractile responses were recorded after dosing with carbachol (a bronchial constrictor) and isoproterenol (a bronchial dilator).

Airway Physiology

Anesthesia was achieved with 60 mg/kg of pentobarbital sodium i.p., neuromuscular blockade with 0.8 ml/kg pancuronium bromide, and ventilation with a computer-controlled small animal ventilator (FlexiVent™, SCIREQ, Montreal, QC, Canada), with a tidal volume of 7.5 ml/kg and a positive end-expiratory pressure of 3 cm $H_2O$. Measurements of respiratory mechanics were made by the forced oscillation technique. Response to aerosolized methacholine (0, 10 mg/ml, 25 mg/ml, and 100 mg/ml) was determined by resistance measurements every 30 seconds for 5 minutes, ensuring the parameters calculated had peaked. The resistance measurements were then averaged at each dose and graphed ($R_T$, measured in cm $H_2O$/ml/s) along with the initial baseline measurement.

Animal Models of AHR

In the following studies to evaluate the effect of oHA, mice were exposed to sHA (50 μl of a 1 mg/ml sHA solution in PBS—sonicated Healon, AMO Inc., Santa Ana, Calif.) or inhaled endotoxin (5 μg/m$^3$) over 2.5 hours. Mice were phenotyped for AHR at typical time points for each of these exposures: 2 hours after sHA instillation; or 4 hours after endotoxin exposure. Thirty minutes prior to phenotyping, mice received appropriate treatment (saline, vehicle or oHA) by oropharyngeal aspiration. Mice were treated with 50 μl of 1.5 mg/ml oHA. Phenotyping was with invasive airway pressure measurements (FlexiVent™).

Results

Hyaluronan oligosaccharides (oHA) have identical basic hyaluronan structure (N-acetyl glucosamine and glucuronic acid) as sHA and native high molecular weight hyaluronan (HMW-HA). However, sHA and HMW-HA consist of hundreds, up to 25,000 disaccharide units, while oHA are only 2-12 disaccharide units long. oHA are thought to engage single HA receptors, and therefore prevent the formation of receptor complexes that are necessary for full HA-mediated effects. oHA have been shown to possess anti-cancer activity, but no effects have been described in AHR.

Figure 5:
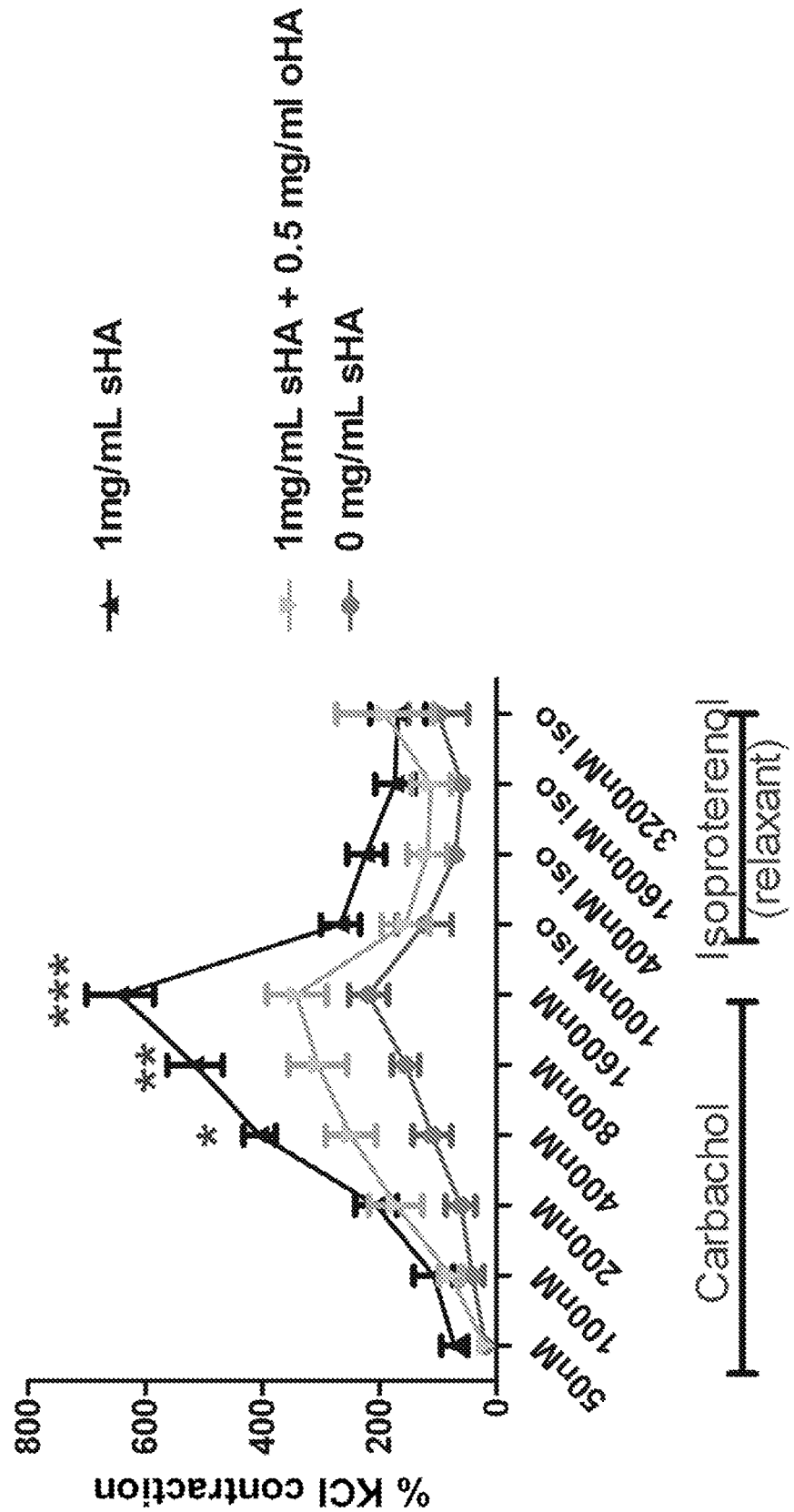
FIG. 5 is a graph showing hyaluronan oligosaccharides (oHAs) ameliorate tracheal ring contractility after sHA exposure using an in vitro model of mouse airway smooth muscle cell (maSMC) contractility. Tracheal rings were excised from euthanized mice, and then mounted on a tension-measuring device. sHA led to an exaggerated contractile response of mouse tracheal rings to the constrictor substance carbachol (1 mg/mL sHA). Addition of oHA inhibited this action (1 mg/mL sHA+0.5 mg/mL oHA), almost to the level of control tracheal rings (0 mg/mL sHA).

The effect of oHA on AHR was evaluated in a tracheal ring assay, an in vitro model of mouse airway smooth muscle cell contractility. Tracheal rings were excised from euthanized mice, and then mounted on a tension-measuring device. As shown in FIG. 5, sHA led to an exaggerated contractile response of mouse tracheal rings to the constrictor substance carbachol (1 mg/mL sHA). Addition of oHA inhibited this action (1 mg/mL sHA+0.5 mg/mL oHA), almost to the level of control tracheal rings (0 mg/mL sHA). These results demonstrate that oHAs ameliorate tracheal ring contractility after sHA exposure in vitro.

Figure 6:
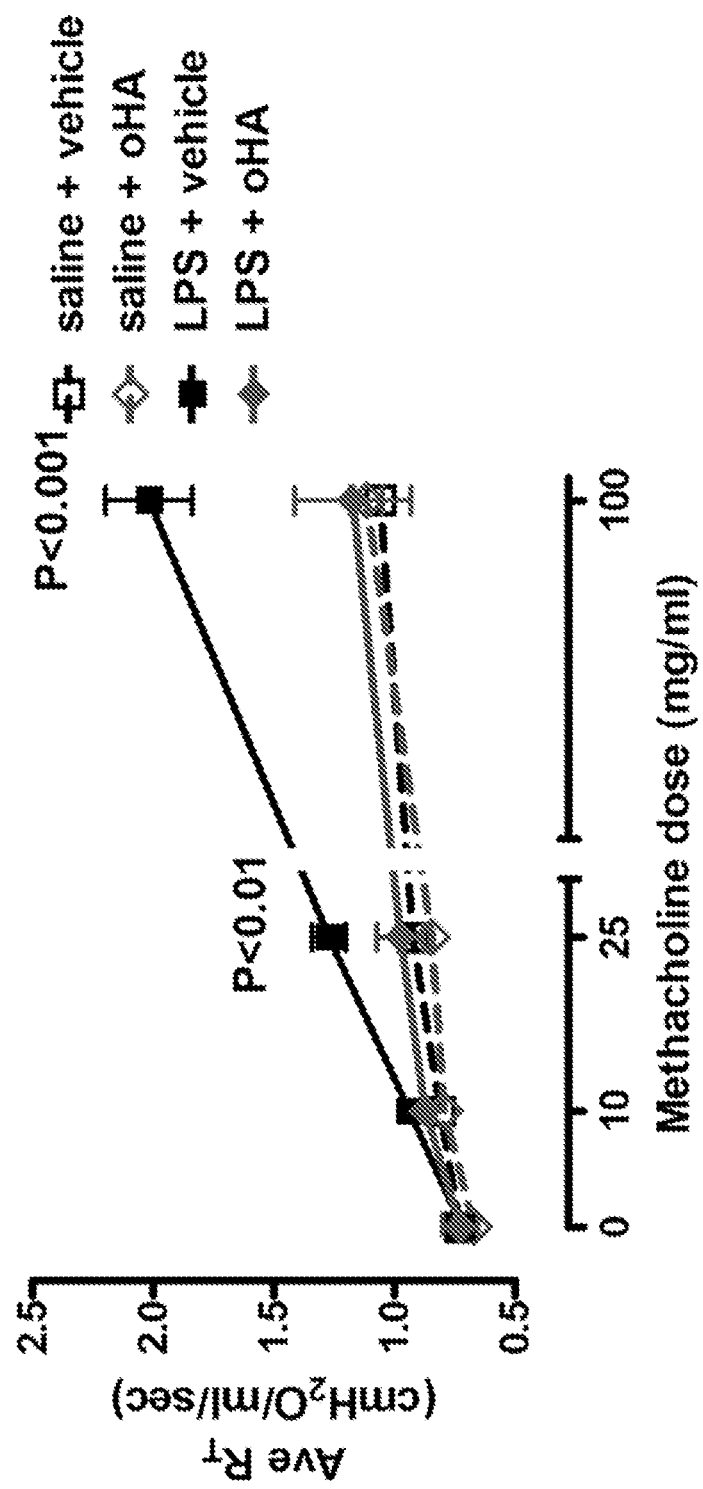
FIG. 6 is a graph showing oHAs abolish inflammatory AHR after inhaled lipopolysaccharide exposure in vivo. Mice were exposed to inhaled endotoxin. Measurement of airway resistance showed that oHA, even when given after the exposure, led to decreased airway resistance (LPS+ oHA), which was comparable to sham-treated (naïve) mice (saline+vehicle). oHA alone had no effect on airway contractility (saline+oHA).

The effect of oHAs on AHR in vivo was also evaluated using a murine model of airway contraction in inflammatory asthma. Mice were exposed to inhaled endotoxin (LPS), which causes airway inflammation and bronchial constriction, and is an accepted model of inflammatory asthma. As shown in FIG. 6, measurement of airway resistance showed that oHA, even when given after the exposure, led to decreased airway resistance (LPS+oHA), which was comparable to sham-treated (naïve) mice (saline+vehicle). oHA alone had no effect on airway contractility (saline+oHA). These results indicate that oHAs abolish inflammatory AHR after inhaled LPS exposure in vivo.

Example 3: Use of Hyaluronan Antagonists in a Guinea Pig Model of AHR

This example describes a guinea pig model that can be used to evaluate the effect of hyaluronan antagonists, such as heparosan and oHA, on the development of AHR in response to ozone. Guinea pig models of AHR have been described in the art (see, for example, Verhein et al., *Am J Respir Cell Mol Biol* 39:730-738, 2008).

Pathogen-free Dunkin-Hartley guinea pigs (Elm Hill Breeding Labs, Chelmsford, Mass.) are exposed to 2 ppm ozone or filtered air for approximately 4 hours (Yost et al., *J Appl Physiol* 87:1272-1278, 1999). Heparosan or oHA is administered intraperitoneally. PBS-injected animals serve as controls. Heparosan or oHA can be administered either before exposure to ozone, during exposure, or following exposure, such as 24 hours after exposure. One to three days following exposure to ozone, animals are anesthetized with urethane (1.9 g/kg, intraperitoneally) and evaluated for AHR according to standard procedures (see Verhein et al., *Am J Respir Cell Mol Biol* 39:730-738, 2008).

Example 4: Use of Hyaluronan Antagonists in Chronic Models of Airway Disease

This example describes animal models that can be used to represent chronic airway disease, such as asthma or COPD.

Animal models of chronic airway disease have been described in the art (see, for example, Savov et al., *Am J Physiol Lung Cell Mol Physiol* 283(5):L952-962, 2002).

Chronic Ozone Exposure

C57BL/6J mice are exposed to either Hepa-filtered air or ozone. Animals are housed in cages with low-endotoxin bedding, and given water and chow ad libitum. Animals are exposed to 0.3 ppm ozone for 72 hours. Exposures are performed in 55-liter Hinner chambers with individual animal slots. Air at 20-22° C. and 50-60% relative humidity is supplied at 20 exchanges per hour. Ozone is generated by directing 100% $O_2$ through a UV light generator, and mixed with air supply to the chamber. Chamber ozone concentration is monitored continuously with a UV light photometer (1003AH, Dasibi, Glendale, Calif.). Heparosan or oHA is administered either daily during exposures, or once at the end of the exposure. Mice are subjected to invasive AHR measurement and euthanized, and subsequently lung tissue is collected.

LPS Exposure

Lyophilized, reconstituted LPS (*Escherichia coli* serotype 0111:B4, Sigma, St. Louis, Mo.) is used. LPS aerosol was generated as previously described (Savov). Briefly, a six-jet Atomizer (Model 9306, TSI Inc., Shoreview, Minn.) is used at a constant pressure of 35 pounds per square inch (psi). Mice are exposed for 2.5 hours (acute exposure), or for 2.5 hours per day, 5 days per week, for one to four weeks (chronic exposure). LPS concentrations are determined by sampling the total chamber outflow, using the quantitative chromogenic *Limulus* amebocyte lysate (LAL) assay (QCL-1000; Whittaker Bioproducts, Walkersville, Md.). The concentrations of LPS aerosol (LAL assay) in these experiments are 6-8 $\mu g/m^3$. Heparosan or oHA is administered either daily during exposures, or once at the end of the exposure. Mice are subjected to invasive AHR measurement and euthanized, and subsequently lung tissue is collected.

Example 5: Dose-Response Studies in Animals to Identify Effective Dose Range

This example describes a method that can used to determine the lowest effective dose of heparosan and/or oHA for the inhibition of AHR.

A/J mice are sensitized to ovalbumin and exposed to inhaled ovalbumin every other day for 4 weeks. Mice receive instilled oHA or heparosan or vehicle control before every treatment. After 4 weeks of treatment, mice undergo evaluation of airway hyperresponsiveness and histological analysis of their lungs for airway remodeling and inflammation to determine what dose is the lowest effective dose for inhibiting AHR. Mice will then be tested at doses 2- to 10-fold greater than the lowest effective dose for chronic exposure experiments to identify an appropriate dose range for chronic (e.g., daily) treatment.

Example 6: Use of Hyaluronan Antagonists in the Treatment of Asthma

This example describes the use of a hyaluronan antagonist, such as heparosan or oHA, in the treatment of asthma.

An individual suffering from asthma is selected for treatment. The subject is administered either heparosan or oHA daily by aerosol, such as by using an appropriate inhaler or nebulizer. A skilled practitioner is capable of selecting an appropriate dose of heparosan or oHA to administer to the subject based on a variety of factors, including age, weight and severity of the asthma. The dose of heparosan or oHA can be adjusted as needed to control the symptoms of asthma.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of treating an acute or chronic airway disease or disorder in a subject, or for preventing or reducing airway hyperresponsiveness (AHR) in a subject, comprising:
   selecting a subject with an acute or chronic airway disease or disorder, or suffering from or at risk for AHR; and
   administering to the subject a therapeutically effective amount of heparosan,
   thereby treating the acute or chronic airway disease or disorder, or preventing or reducing AHR in the subject.

2. The method of claim 1, wherein the subject has a chronic airway disease or disorder.

3. The method of claim 2, wherein the chronic disease or disorder comprises one or more of asthma, chronic obstructive pulmonary disease, cystic fibrosis, obliterative bronchiolitis, diffuse panbronchiolitis or cryptogenic organizing pneumonia.

4. The method of claim 1, wherein the airway disease or disorder is an acute disease or disorder.

5. The method of claim 4, wherein the acute disease or disorder comprises one or more of exercise-induced asthma, respiratory infection, acute bronchiolitis, airway hyperresponsiveness, pollution-induced airway injury, chemical-induced airway injury or ventilation-induced airway injury.

6. The method of claim 1, wherein AHR is triggered by an environmental trigger, a chemical trigger, exertion or stress.

7. The method of claim 6, wherein the environmental trigger is ozone, particulate matter or an allergen.

8. The method of claim 6, wherein the heparosan is administered prophylactically prior to exposure to the trigger.

9. The method of claim 1, wherein the heparosan is formulated for local delivery to the airway.

10. The method of claim 9, wherein local delivery comprises aerosol delivery.

11. The method of claim 10, wherein the heparosan is formulated for aerosol delivery using an inhaler.

12. The method of claim 11, wherein the inhaler is a dry powder inhaler.

13. The method of claim 11, wherein the inhaler is a metered-dose inhaler.

14. The method of claim 10, wherein the heparosan is formulated for aerosol delivery using a nebulizer.

15. The method of claim 1, wherein the heparosan is administered daily.

16. The method of claim 1, wherein the heparosan is administered at a dose of about 1 to about 100 µg.

17. The method of claim 1, wherein the heparosan administered at a dose of about 10 to about 50 µg.

* * * * *

UNITED STATES PATENT AND TRADEMARK OFFICE
CERTIFICATE OF CORRECTION

PATENT NO.       : 9,717,752 B2
APPLICATION NO.  : 14/398837
DATED            : August 1, 2017
INVENTOR(S)      : Garantziotis et al.

It is certified that error appears in the above-identified patent and that said Letters Patent is hereby corrected as shown below:

On the Title Page

Item (72) Inventors should read:
Stavros Garantziotis, Chapel Hill, NC (US);
John W. Hollingsworth, Durham, NC (US);
Jian Liu, Chapel Hill, NC (US)

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*